US009891229B2

(12) United States Patent
Saeki et al.

(10) Patent No.: US 9,891,229 B2
(45) Date of Patent: Feb. 13, 2018

(54) METHOD FOR DETERMINING UBIQUITIN CHAIN LENGTH

(71) Applicant: Tokyo Metropolitan Institute of Medical Science, Tokyo (JP)

(72) Inventors: Yasushi Saeki, Tokyo (JP); Hikaru Tsuchiya, Tokyo (JP); Ai Kaiho, Tokyo (JP); Keiji Tanaka, Tokyo (JP)

(73) Assignee: Tokyo Metropolitan Institute of Medical Science, Tokyo (JP)

( * ) Notice: Subject to any disclaimer, the term of this patent is extended or adjusted under 35 U.S.C. 154(b) by 0 days.

(21) Appl. No.: 15/711,432

(22) Filed: Sep. 21, 2017

(65) Prior Publication Data

US 2018/0017571 A1 Jan. 18, 2018

Related U.S. Application Data

(62) Division of application No. 14/533,182, filed on Nov. 5, 2014.

(60) Provisional application No. 61/901,452, filed on Nov. 8, 2013.

(51) Int. Cl.
*G01N 33/68* (2006.01)
*C07K 14/47* (2006.01)

(52) U.S. Cl.
CPC ..... *G01N 33/6842* (2013.01); *C07K 14/4702* (2013.01); *G01N 33/6803* (2013.01)

(58) Field of Classification Search
None
See application file for complete search history.

(56) References Cited

U.S. PATENT DOCUMENTS

2009/0220470 A1 9/2009 Medina et al.

OTHER PUBLICATIONS

Hjerpe, Ret al., "Efficient Protection and Isolation of Ubiquitylated Proteins Using Tandem Ubiquitin-Binding Entities", EMBO reports 10, 1250-1258, doi:10.1 038/embor.2009.192, 2009.
Takayoshi Kirisako et al., "A Ubiquintin Ligase Complex Assembles Linear Polyubiquitin Chains", The EMBO Journal25, 4877-4887, 2006.
Elsasser_ S. et al. "Protaesome Subunit RPN1 Binds Ubiquitin-like Protein Domains", Nature cell biology 4, 725-730, 2002.
Matsuda, N. et ai.,"Protein Synthesis, Post-Translation Modification, and Degradation", The Journal of biological chemistry 281, 3204-3209, 2006.
Tsuchiya, H, et al., "The Parallel Reaction Monitoring Method Contributes to a Highly Sensitive Polyubiquitin Chain Quantification", Biochemical and biophysical research communications 436, 223-229, 2013.
Ziv I. et al., "A perturbed Ubiquitin Landscape Distinguishes between Ubiquitin in Trafficking and in Proteolysis", Molecular & cellular proteomics: MCP 10, M111 009753, 2011.
Danielle L Swaney et al., "The Valueo f Using Multiple Proteases for Large-Scale Mass Specrrometry-Based Proeomics", Journal of proteome research 9, 1323-1329,2010.
Stephen E Kaiser et al., "Protein Standard Absolute Quantification (PSAQ) Method for the Measurement of Cellular Obiquitin Pools", Nature methods 8, 691-696, 2011.
Hershko, A. et al., "The ubiquitin system", Annual review of biochemistry 67, 425-479, 1998.
Daniel Finley et al., "Ubiquitin As a Central Cellular Regulator", Cell, 116, S29-32, 22 p following S32, 2004.
Rasmus Hartmann-Petersen et al., "Ubiquitin Binding Proteins Protect Ubiquitin Conjugates from Disassembly" FEBS letters 535, 77-81, 2003.
Holger Richly et al., "A Series of Ubiquitin Binding Factors Connects CDC48/P97 to Substrate Multiubiquitylation and Proteasonmal Targeting", Cell, 120, 73-84, 2005.
Pierce, N. W. et al., "Detection of Sequential Polyubiquitylation on a Millisecond Timescale", Nature 462, 615-619, 2009.
Komander, D. et al., "The Ubiquitin Code" Annual review of biochemistry 81, 203-229, 2012.

(Continued)

*Primary Examiner* — Suzanne M Noakes
(74) *Attorney, Agent, or Firm* — Thomas|Horstemeyer LLC

(57) ABSTRACT

Protein ubiquitylation, an essential post-translational modification, regulates almost every cellular process including protein degradation, protein trafficking, signal transduction, and DNA damage response in eukaryotic cells. The diverse functions of ubiquitylation are thought to be mediated by distinct chain topologies resulting from eight different ubiquitin linkages, chain lengths, and complexities. Currently, ubiquitin linkages are generally thought to be a critical determinant of ubiquitin signaling. However, ubiquitin chain lengths, another key element of ubiquitin signaling, have not been well documented especially in vivo situation during past three decades from the discovery of ubiquitin. The reason of this was simply because no method has been available for determination of ubiquitin chain length in endogenous ubiquitylated substrates. In the present invention, a practical technique for determining the actual length of substrate-attached polyubiquitin chains from biological samples is established. Using the method, the mean length of substrate-attached polyubiquitin chains was determined and the robustness of ubiquitin chain length regulation in cells is investigated. The following is a summary of findings in this invention: 1. A method for determining ubiquitin chain length was developed and this method was named 'ubiquitin protection from trypsinization' (Ub-ProT). 2. Using Ub-ProT, it was determined that the mean length of substrate-attached ubiquitin chains is in the dimer to decamer range. 3. By quantitative proteomics, it was found that the mean lengths of five major types of ubiquitin chains can be divided into two groups. 4. Proteasome-inhibition did not alter the mean length of substrate-attached polyubiquitin chains, indicating that cells have a robust system for regulating ubiquitin chain length.

2 Claims, 13 Drawing Sheets

(56) References Cited

OTHER PUBLICATIONS

Grabbe, C. et al., "The Spatial and Temporal Organization of Ubiquitin Networks", Molecular cell biology 12, 295-307, 2011.
Thrower, J. S. et al., "Recognition of the Polyubiquitin Proteolytic Signal", The EMBO Journal19, 94-102, 2000.
Rape, M. et al., "The Processivity of Multiubiquitination by the APC Determines the Order of Substrate Degradation", Cell124, 89-103, 2006.
Saeki, Y. et al., "Ubiquitin-Like Proteins and RPN10 Play Cooperative Roles in Ubiquitin-Dependent Proeolysis", Biochemical and biophysical research communications 293, 986-992, 2002.
Raasi, S. et al., "Protein Synthesis Post-Translation Modificaiton and Degradation: Rad23 Ubiquitin-Associated Domains (UBA) Inhibit 26 S Sequestering Lysine 48 Linked Polyubiquintin Chains", The Journal of biological chemistry 278,8951-8959,2003.
Wilkinson, C. R. et al., "Proteins containing the UBA Domain are Able to Bind to Multi-Ubiquintin Chains", Nature cell biology 3, 939-943, 2001.
Ikeda, F. et al., "What Determines the Specificity and Outcomes of Ubiquitin Signaling?" Cell143, 677-681, 2010.
Kirkpatrick, D. S. et al., "Quantitative Analysis of in Vitro Ubiquitinated Cyclin 81 Reveals Complex Chain Topology", Nature cell biology 8, 700-71 0, 2006.
Phu, L. et al., "Improved Quantitative Mass Spectrometry Methods for Characterizing Complex Ubiquitin Signals", Molecular & cellular proteomics: MCP 10, M110.003756, 2011.
Carrano, A. C. et al., "Using the Ubiquitin-Modified Proteome to Monitor Protein Homeostasis Function", Molecular & Cellular proteomics : MCP, 3521-3531, 2013.
Newton, K. et al. "Ubiquitin Chain Editing Revealed by Polyubiquitin Linkage-Specific Antibodies", Cell134, 668-678, 2008.
Kim, H. T. et al., Protein Synthesis, Post-Translation Modification, and Degradation: Certain Pairs of Ubiquitin-conjugating Enzymes (E2S) and Ubiquitin-Protein Ligases (E3s) Synthesize Nondegradable Forked Ubiquitin Chains containing all Possible Isopeptide Linkages . . . The Journal of biological chemistry 282,17375-17386, 2007.
Sarraf, S. A. et al., "Landscaped of the Parkin-dependent Ubiquitylome in Response to Mitochondrial Depolarization", Nature 496, 372-376, 2013.
Peng, J. et al., "A Protein Approach to Understanding Protein Ubiquitination", Nature biotechnology 21, 921-926,2003.
Saeki, Y. et al "Lysine 63-linked polyubiquitin chain may serve as a targeting signal for the 26S proteasome", The EMBO Journal 28, 359-371,2009.
Peterson, A. C. et al., Parallel Reaction Monitoring for High Resolution and High Mass Accuracy Quantitative, Targeted Proteomics, Molecular & cellular proteomics, MCP 11, 1475-1488,2012.
Fleming, J. A. et al. "Complementary whole-genome technologies reveal the cellular response to proteasome inhibition by PS-341 ", Proceedings of the National Academy of Sciences of the United States of America 99,1461-1466, 2002.
Ozkaynak, E. et al., "The yeast ubiquitin genes: a family of natural gene fusions", The EMBO Journal 6, 1429-1439, 1987.
Chen, Y. et al., "Consequences of the overexpression of ubiquitin in yeast: elevated tolerances of osmostress, ethanol and canavanine, yet reduced tolerances of cadmium, arsenite and paromomycin", Biochimica et biophysics acta 1268, 59-64, 1995.
Meyer, H. et al., "Emerging functions of the VCP/p97 AAA-ATPase in the ubiquitin system", Nature cell biology 14, 117-123, 2012.
Hanna, J. et al., "Deubiquitinating Enzyme Ubp6 Functions Noncatalytically to Delay Proteasomal Degradation", Cell 127, 99-111, doi: 10.1 016/j.ce11.2006.07.038, 2006.
Kolawa, N. et al. "Perturbations to the Ubiquitin Conjugate Proteome in Yeast ubx Mutants Identify Ubx2 as a Regulator of Membrane Lipid Composition", Molecular & cellular proteomics MCP, doi:10.1074/mcp.MII3.030163, 2013.
Gavin, A. C. et al. "Proteome survey reveals modularity of the yeast cell machinery", Nature 440, 631-636, 2006.
Bagola, K. et al. "Ubiquitin Binding by a CUE Domain Regulates Ubiquitin Chain Formation by ERAD E3 Ligases", Molecular cell 50, 528-539, 2013.
Sherman, F., "Getting Started with Yeast", Methods in enzymology 194, 3-21, 1991.
Hicke et al., Ubiquitin-Binding Domains, Nature Reviews, vol. 6, p. 610-621, Aug. 2005.
Husnjak et al., Ubiquitin-Binding Proteins: Decoders of Ubiquitin-Mediated Cellular Functions, Annu. Rev. Blochem, 81:291-322, 2012.
Correction to Previously Cited Reference Kirkpatrick, D. S. et al., "Quantitative Anaylsis of in Vitro Ubiquitinated Cyclin B1 Reveals Complex Chain Topolgy", Nature cell biology 8, 700-71 0, 2006.
Office Action issued by the U.S. Patent Office for U.S. Appl. No. 14/533,182, dated Dec. 2, 2016.
Office Action issued by the U.S. Patent Office for U.S. Appl. No. 14/533,182, dated Mar. 31, 2017.
Notice of Allowance issued by the U.S. Patent Office for U.S. Appl. No. 14/533,182, dated Oct. 3, 2017.

SEQUENCE LISTING

```
<160> NUMBER OF SEQ ID NOS: 4

<210> SEQ ID NO 1
<211> LENGTH: 385
<212> TYPE: PRT
<213> ORGANISM: Artificial Sequence
<220> FEATURE:
<223> OTHER INFORMATION: Synthetic Construct

<400> SEQUENCE: 1

Met Arg Gly Cys His His His His His His Gly Met Ala Ser Met Thr
1               5                   10                  15

Gly Gly Gln Gln Met Gly Asp Ile Gly Gly Gly Gly Ser Gly Gly Gly
            20                  25                  30

Val Asn Pro Gln Leu Gln Asn Pro Glu Val Ala Phe Gln Gln Gln Leu
        35                  40                  45

Glu Gln Leu Ser Ala Met Gly Phe Leu Asn Ala Glu Ala Asn Leu Gln
    50                  55                  60

Ala Leu Ile Ala Thr Gly Gly Asp Ile Asn Ala Ala Ile Glu Ala Leu
65                  70                  75                  80

Leu Gly Ser Gln Pro Ser Gly Gly Gly Gly Ser Gly Gly Gly Val Asn
                85                  90                  95

Pro Gln Leu Gln Asn Pro Glu Val Ala Phe Gln Gln Gln Leu Glu Gln
            100                 105                 110

Leu Ser Ala Met Gly Phe Leu Asn Ala Glu Ala Asn Leu Gln Ala Leu
        115                 120                 125

Ile Ala Thr Gly Gly Asp Ile Asn Ala Ala Ile Glu Ala Leu Leu Gly
    130                 135                 140

Ser Gln Pro Ser Gly Gly Gly Gly Ser Gly Gly Gly Val Asn Pro Gln
145                 150                 155                 160

Leu Gln Asn Pro Glu Val Ala Phe Gln Gln Gln Leu Glu Gln Leu Ser
                165                 170                 175

Ala Met Gly Phe Leu Asn Ala Glu Ala Asn Leu Gln Ala Leu Ile Ala
            180                 185                 190

Thr Gly Gly Asp Ile Asn Ala Ala Ile Glu Ala Leu Leu Gly Ser Gln
        195                 200                 205

Pro Ser Gly Gly Gly Gly Ser Gly Gly Gly Val Asn Pro Gln Leu Gln
    210                 215                 220

Asn Pro Glu Val Ala Phe Gln Gln Gln Leu Glu Gln Leu Ser Ala Met
225                 230                 235                 240
```

-continued

```
Gly Phe Leu Asn Ala Glu Ala Asn Leu Gln Ala Leu Ile Ala Thr Gly
                245                 250                 255

Gly Asp Ile Asn Ala Ala Ile Glu Ala Leu Leu Gly Ser Gln Pro Ser
            260                 265                 270

Gly Gly Gly Gly Ser Gly Gly Gly Val Asn Pro Gln Leu Gln Asn Pro
        275                 280                 285

Glu Val Ala Phe Gln Gln Gln Leu Glu Gln Leu Ser Ala Met Gly Phe
    290                 295                 300

Leu Asn Ala Glu Ala Asn Leu Gln Ala Leu Ile Ala Thr Gly Gly Asp
305                 310                 315                 320

Ile Asn Ala Ala Ile Glu Ala Leu Leu Gly Ser Gln Pro Ser Gly Gly
                325                 330                 335

Ala Phe Gln Gln Gln Leu Glu Gln Leu Ser Ala Met Gly Phe Leu Asn
            340                 345                 350

Ala Glu Ala Asn Leu Gln Ala Leu Ile Ala Thr Gly Gly Asp Ile Asn
        355                 360                 365

Ala Ala Ile Glu Ala Leu Leu Gly Ser Gln Pro Ser Gly Gly Gly Gly
    370                 375                 380

Ser
385
```

<210> SEQ ID NO 2
<211> LENGTH: 1206
<212> TYPE: DNA
<213> ORGANISM: Artificial Sequence
<220> FEATURE:
<223> OTHER INFORMATION: Synthetic Construct

<400> SEQUENCE: 2

```
atgcggggtt gtcatcatca tcatcatcat ggtatggcta gcatgactgg tggacagcaa      60

atgggtgata tcggaggtgg aggatctgga ggtggagtaa atcctcagct acagaatcca     120

gaagtcgcgt ttcagcaaca actggaacaa ctcagtgcaa tgggattttt gaacgcggaa     180

gcaaacttgc aagctctaat agcaacagga ggtgatatta atgcagctat tgaagcgtta     240

ctgggctccc agccatcagg aggtggagga tctggaggtg gagtaaatcc tcagctacag     300

aatccagaag tcgcgtttca gcaacaactg gaacaactca gtgcaatggg atttttgaac     360

gcggaagcaa acttgcaagc tctaatagca acaggaggtg atattaatgc agctattgaa     420

gcgttactgg gctcccagcc atcaggaggt ggaggatctg gaggtggagt aaatcctcag     480

ctacagaatc cagaagtcgc gtttcagcaa caactggaac aactcagtgc aatgggattt     540

ttgaacgcgg aagcaaactt gcaagctcta atagcaacag gaggtgatat taatgcagct     600

attgaagcgt tactgggctc ccagccatca ggaggtggag gatctggagg tggagtaaat     660

cctcagctac agaatccaga agtcgcgttt cagcaacaac tggaacaact cagtgcaatg     720

ggatttttga acgcggaagc aaacttgcaa gctctaatag caacaggagg tgatattaat     780

gcagctattg aagcgttact gggctcccag ccatcaggag gtggaggatc tggaggtgga     840

gtaaatcctc agctacagaa tccagaagtc gcgtttcagc aacaactgga acaactcagt     900

gcaatgggat ttttgaacgc ggaagcaaac ttgcaagctc taatagcaac aggaggtgat     960

attaatgcag ctattgaagc gttactgggc tcccagccat caggaggtgg aggatctgga    1020

ggtggagtaa atcctcagct acagaatcca gaagtcgcgt ttcagcaaca actggaacaa    1080

ctcagtgcaa tgggattttt gaacgcggaa gcaaacttgc aagctctaat agcaacagga    1140
```

-continued

```
ggtgatatta atgcagctat tgaagcgtta ctgggctccc agccatcagg aggtggagga   1200

tcctaa                                                              1206


<210> SEQ ID NO 3
<211> LENGTH: 7
<212> TYPE: PRT
<213> ORGANISM: Artificial Sequence
<220> FEATURE:
<223> OTHER INFORMATION: Synthetic Construct

<400> SEQUENCE: 3

Gly Gly Gly Ser Gly Gly Gly
1               5


<210> SEQ ID NO 4
<211> LENGTH: 8
<212> TYPE: PRT
<213> ORGANISM: Artificial Sequence
<220> FEATURE:
<223> OTHER INFORMATION: Synthetic Construct

<400> SEQUENCE: 4

Gly Gly Gly Gly Ser Gly Gly Gly
1               5
```

METHOD FOR DETERMINING UBIQUITIN CHAIN LENGTH

CROSS-REFERENCE TO RELATED APPLICATION

The present application is a divisional of copending application Ser. No. 14/533,182, filed Nov. 5, 2014, which claims the benefit of U.S. Provisional Patent Application No. 61/901,452, filed Nov. 8, 2013, the content of which is incorporated herein by reference.

FIELD OF THE INVENTION

The present invention relates to the field of ubiquitin analysis. In particular, the present invention relates to the method for determining ubiquitin chain length, which reveals functional units of polyubiquitin chains in cells.

SEQUENCE LISTING(S)

This application contains a sequence listing filed in electronic form as an ASCII.txt file entitled 02105066.txt, created on Oct. 31, 2014, and having a size of 5321 bytes. The content of the sequence listing is incorporated herein in its entirety.

BACKGROUND OF THE INVENTION

Protein ubiquitylation is an essential post-translational modification responsible for a diverse array of cellular processes, including protein degradation, protein trafficking, signal transduction, and the DNA damage response. Ubiquitylation is catalyzed by the concerted action of ubiquitin activating (E1), ubiquitin conjugating (E2), and ubiquitin ligase (E3) enzymes. Deubiquitylating (DUB) enzymes antagonize ubiquitylation by removing ubiquitin modifications from their substrates. Ubiquitin can be covalently conjugated to substrates in several ways: as single ubiquitin conjugated to a single site (monoubiquitylation) or multiple sites (multiple monoubiquitylation), or as a polymeric chain (polyubiquitylation). Ubiquitin can form various isopeptide linkages with itself via seven internal lysine (K) residues as well as its N-terminal methionine (M1). In addition to the homogeneous chains, it has been assumed that cells contain heterogeneous chains, such as forked or mixed chains that contain multiple types of linkages.

Accumulating evidence has suggested that the various functions of ubiquitylation are mediated by distinct chain topologies with eight different ubiquitin linkages, lengths, and complexities (FIG. 1). Of these, the linkage types are generally thought to be a critical determinant of chain function. It is widely accepted that K48-linked chains function as targeting signals for proteasomal destruction, whereas K63-linked chains are usually involved in DNA repair and the trafficking of membrane proteins. The functions of atypical chains linked through M1, K6, K11, K27, K29, or K33 are only beginning to be understood, and the roles of mixed and branched chains are unknown. Ubiquitin binding domain (UBD)-containing proteins, many of which exhibit preferences for specific ubiquitin chain types or lengths, play key roles in decoding the signals embedded in the structure of ubiquitin chains. Previous in vitro studies have shown that tetraubiquitin is the minimal recognition signal for proteasomal degradation of folded proteins. In this regard, ubiquitin ligases such as SCF and APC can build long polyubiquitin chains processively to ensure rapid degradation of their substrates. Furthermore, Rad23 and Dsk2, extrinsic ubiquitin receptors of the proteasome, preferentially bind polyubiquitin chains with four or more ubiquitins in vitro.

To understand the biological significance of different ubiquitin chain topologies, it is essential to dissect the types of ubiquitin linkages, chain complexities, and chain lengths of endogenous ubiquitylated substrates. Recent advances in mass spectrometry and antibody engineering technologies allow to determine and quantitate ubiquitin linkages in biological complex samples. In addition, the chain complexity of mixed or branched chains can be analyzed by ubiquitin linkage quantitation. By contrast, the length of substrate-attached ubiquitin chains has been analyzed only by gel mobility shift (FIG. 2). However, because most endogenous substrates have multiple ubiquitylation sites and the attached chains have intrinsically heterogeneous lengths, currently, there is no practical technique for determining the actual chain length of endogenous ubiquitylated substrates. Here a novel biochemical method for determining ubiquitin chain length is described. Using this method, the mean length of the substrate-attached polyubiquitin chains and the robustness of ubiquitin length regulation in cells were investigated.

PRIOR ART DOCUMENT

[Patent Document 1] US 2009/0220470 A1

SUMMARY OF THE INVENTION

An object of the present invention is to provide a method for determining ubiquitin chain length, which reveals functional units of polyubiquitin chains in cells, and a polypeptide which is used in the method.

The present inventors have conducted an intensive an extensive study in order to solve the above problems. As a result, the present inventors have found that a polypeptide comprising ubiquitin binding domains having trypsin-resistance is useful for the method for determining ubiquitin chain length, and the present invention was completed.

According to the present invention, the following aspects are provided.

(1) A polypeptide comprising ubiquitin binding domains, wherein said ubiquitin binding domains are linked to each other via a linker amino acid sequence, and wherein the ubiquitin binding domains are protected from trypsinization.

(2) A polypeptide comprising ubiquitin binding domains, wherein said ubiquitin binding domains are linked to each other via a linker amino acid sequence, and wherein the ubiquitin binding domains are trypsin-resistant.

(3) The polypeptide according to (1) or (2), wherein the polypeptide comprises at least four ubiquitin binding domains.

(4) The polypeptide according to any one of (1) to (3), wherein the polypeptide comprises eight or less ubiquitin binding domains.

(5) The polypeptide according to any one of (1) to (4), wherein the ubiquitin binding domain is selected from a group consisting of UBA, UIM, MIU, DIUM, CUE, NZF, A20 ZnF, UBP ZnF, UBZ, UEV, PFU, GLUE, GAT, Jab/MPN, UBM, Ubc, functionally equivalent variant of the aforementioned ubiquitin binding domains, and combinations thereof.

(6) The polypeptide according to any one of (1) to (5), wherein said linker amino acid sequence is a flexible linker sequence.

(7) The polypeptide according to any one of (1) to (6), wherein said linker amino acid sequence is GGGSGGG (SEQ ID NO:3).

(8) The polypeptide according to any one of (1) to (7), wherein said polypeptide further comprises a tag amino acid sequence.

(9) The polypeptide according to (8), wherein said tag is selected from a group consisting of a detection tag, a purification tag, and combinations thereof.

(10) The polypeptide according to (8) or (9), wherein the tag is a biotin tag, a polyhistidine, or a flag tag.

(11) The polypeptide according to any one of (1) to (10), wherein said ubiquitin binding domains are the same or different.

(12) The polypeptide according to any one of (1) to (11), wherein said polypeptide comprises a polypeptide sequence represented by SEQ ID No:1.

(13) The polypeptide according to any one of (1) to (11), wherein a polypeptide sequence has 95% or more homology with the polypeptide sequence represented by SEQ ID No:1.

(14) A polynucleotide comprising a polynucleotide sequence represented by SEQ ID No:2.

(15) A polynucleotide comprising a polynucleotide sequence having 95% or more homology with the polynucleotide sequence represented by SEQ ID No:2.

(16) A gene construct comprising the polynucleotide according to (14) or (15).

(17) An expression vector comprising the gene construct according to (16).

(18) The expression vector according to (17), wherein the gene construct is operatively bound to transcription, and optionally translation, control elements.

(19) The expression vector according to (18), wherein an expression of the gene construct is externally controlled.

(20) The expression vector according to (19), wherein the expression of said gene construct is externally controlled using IPTG.

(21) A method for determining ubiquitin chain length using the polypeptide according to any one of (1) to (13).

(22) The method for determining ubiquitin chain length according to (21) which comprises:

(i) preparing a mixture of an analyte and the polypeptide according to any one of (1) to (13), (ii) digesting the mixture with a protease to form a digested mixture, and (iii) analyzing the digested mixture.

(23) The method for determining ubiquitin chain length according to (22), wherein the protease is trypsin.

(24) The method for determining ubiquitin chain length according to (22) or (23), wherein the digested mixture is analyzed by electrophoresis.

(25) The method for determining ubiquitin chain length according to any one of (22) to (24), wherein the digested mixture is analyzed by western blotting analysis.

(26) The method for determining ubiquitin chain length according to (25), wherein an anti-ubiquitin antibody is used in the western blotting analysis.

(27) The method for determining ubiquitin chain length according to any one of (22) to (26), wherein the mixture further comprises a proteasome inhibitor.

(28) The method for determining ubiquitin chain length according to (27), wherein the proteasome inhibitor is MG132.

(29) A host cell comprising:

(i) the polynucleotide according to (14) or (15);

(ii) the gene construct according to (16); or (iii) the expression vector according to any one of (17) to (20).

(30) The host cell according to (29), wherein said cell is a bacterial cell.

(31) A kit comprising the polypeptide according to any one of (1) to (13).

(32) The kit according to (31), further comprising a solid support.

(left) The structure of ubiquitin. Amino acid residues for polyubiquitylation, seven Lys (K) residues and the $1^{st}$ Met (M1), are indicated.

(right) All the ubiquitin-chain topologies can be divided into three elements, eight different ubiquitin linkages, lengths, and complexities. All of them contribute the ubiquitin function.

Figure 2:
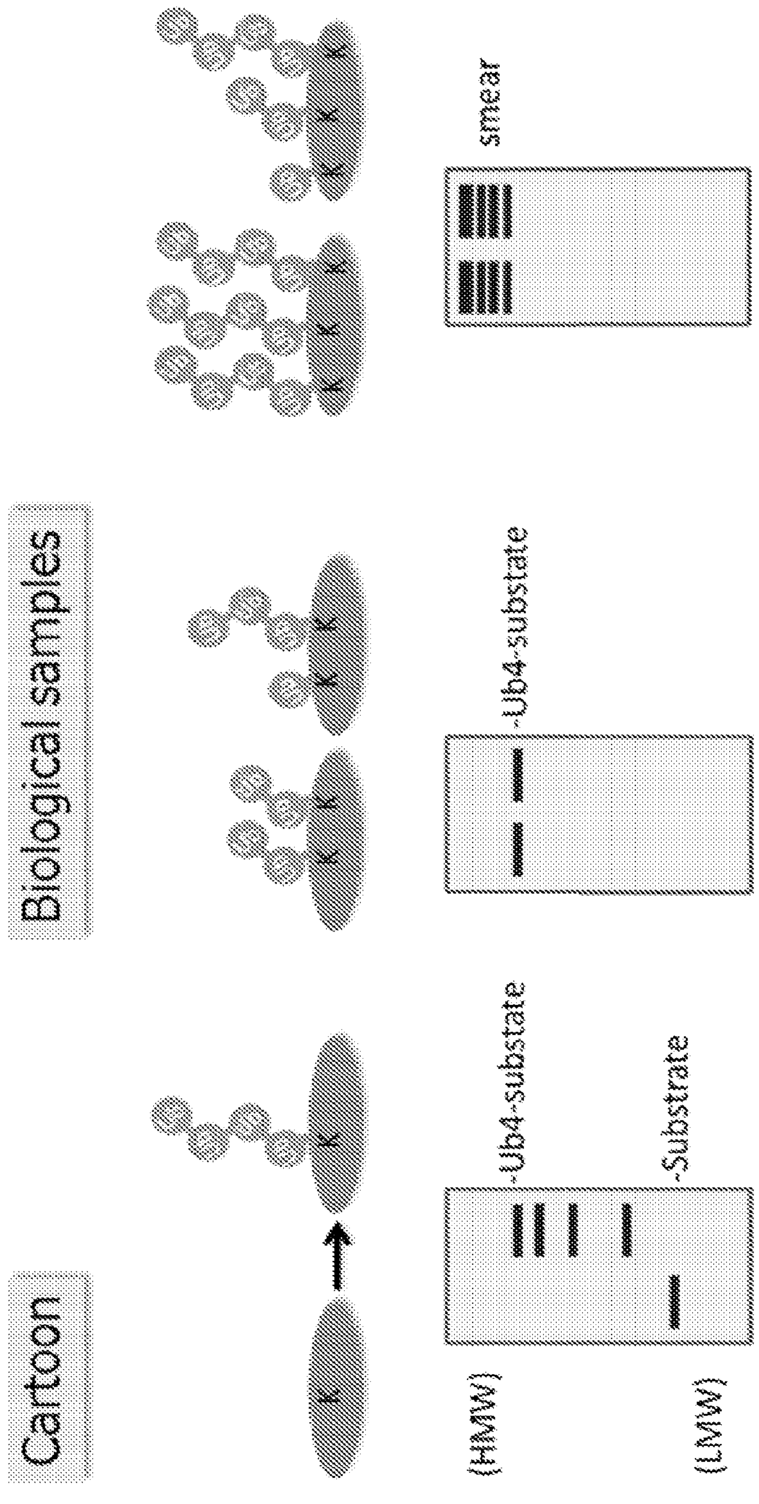

FIG. 2: Estimation of ubiquitin chain length by gel mobility on SDS-PAGE is limited. By analyzing gel mobility on SDS-PAGE analysis, the chain length can be estimated for ubiquitinated proteins with a single ubiquitin chains as in the cartoon. However, most endogenous substrates have multiple ubiquitylation sites and the attached chains have intrinsically heterogeneous lengths. Because of this reason, the SDS-PAGE analysis is not practical technique for determining the actual chain length of endogenous ubiquitylated substrates, i.e., three possible ubiquitinated substrates with four ubiquitin molecules, a single tetra-ubiquitin chain, two di-ubiquitin chains, and mono-ubiquitin and a tri-ubiquitin chain, are not distinguished by their gel mobilities. Furthermore, highly ubiquitinated substrates are detected as smear.

Figure 3A:
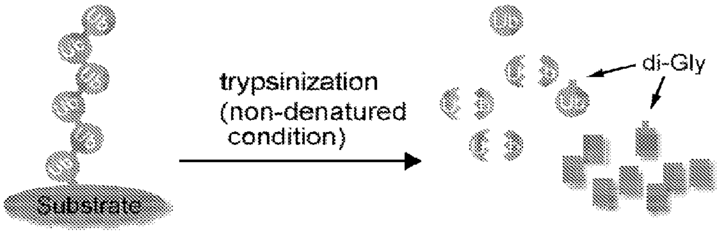
Figure 3B:
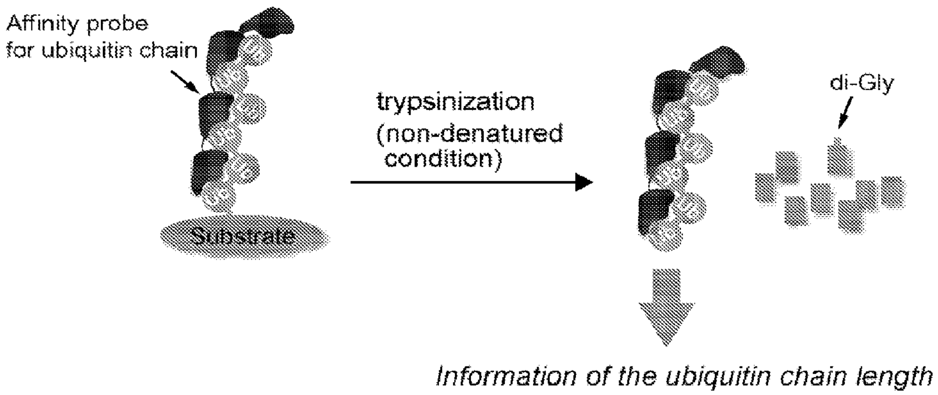

FIGS. 3A and 3B demonstrate one embodiment of a method for determining the chain length of substrate-attached polyubiquitin chains. Trypsinization of the polyubiquitylated substrates under non-denaturing condition results in complete digestion of substrate proteins and partial digestion of ubiquitin chains (FIG. 3A). In the presence of affinity probe for polyubiquitin chains, the polyubiquitin chain would be protected from trypsinization (FIG. 3B). For the purpose, we developed a novel affinity probe, named trypsin-resistant tandem ubiquitin binding entity (TR-TUBE).

Figure 4:
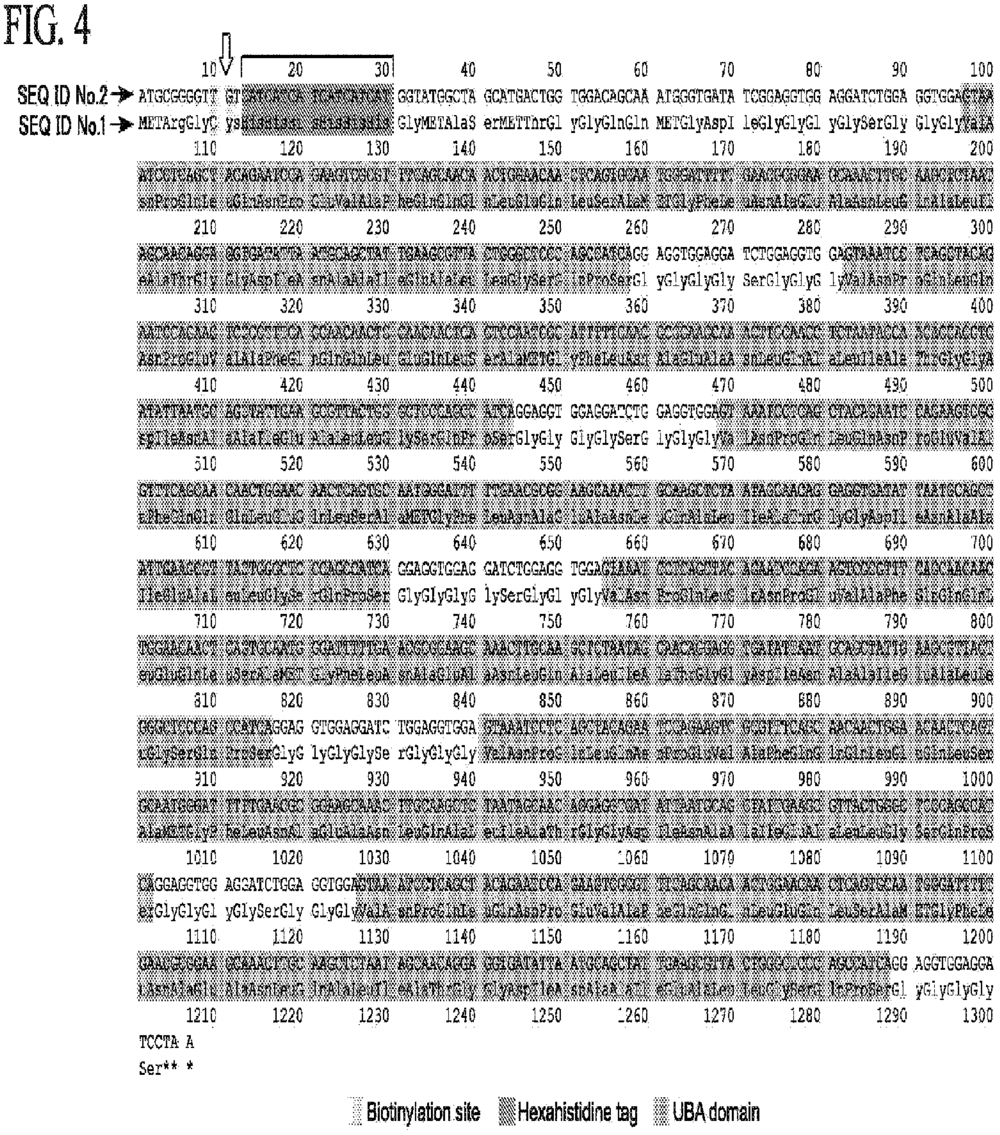

FIG. 4: DNA and protein sequences of TR-TUBE.

TR-TUBE contains a Cys residue (shown by an arrow) for biotinylation, a hexahistidine tag (shown by a frame) for purification, and six tandem repeats of the UBA domain (gray) for high-affinity capture of polyubiquitin chains. Mutated Ala residues within the UBA domain are indicated at 127-129, 175-177, 235-237, 313-315, 361-363, 421-423, 499-501, 547-549, 607-609, 685-687, 733-735, 793-795, 871-873, 919-921, 979-981, 1057-1059, 1105-1107 and 1165-1167.

Figure 5A:
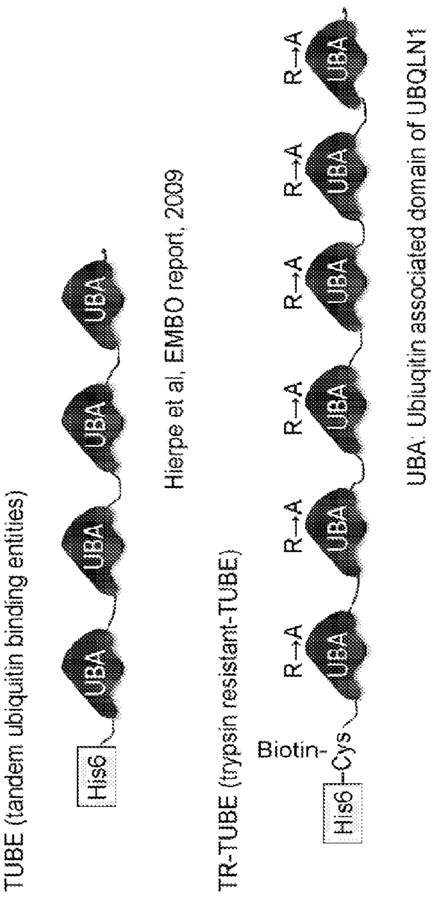
Figure 5B:
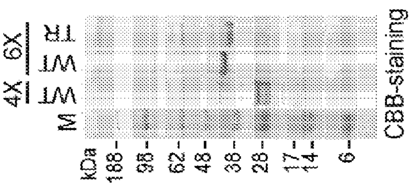
Figure 5C:
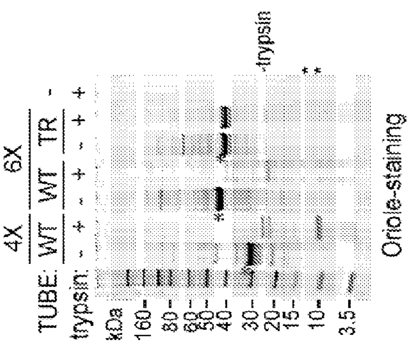

FIGS. 5A-5C demonstrate one embodiment of the construction of TR-TUBE. Illustrations of the original TUBE construct developed by Hierpe et al (EMBO reports 10, 1250-1258, doi:10.1038/embor.2009.192 (2009)), which contains four tandem repeats of the UBA domain of human UBQLN1 (top), and of TR-TUBE, developed in this study (bottom) (FIG. 5A). Expression and purification of 4XTUBE, 6XTUBE, and 6XTR-TUBE. The purified proteins were analyzed by SDS-PAGE (FIG. 5B). Trypsin digestion of TUBEs. The purified TUBEs (1 μg) indicated by asterisks were incubated with trypsin (200 ng) overnight at 37° C. (FIG. 5C).

Figure 6:
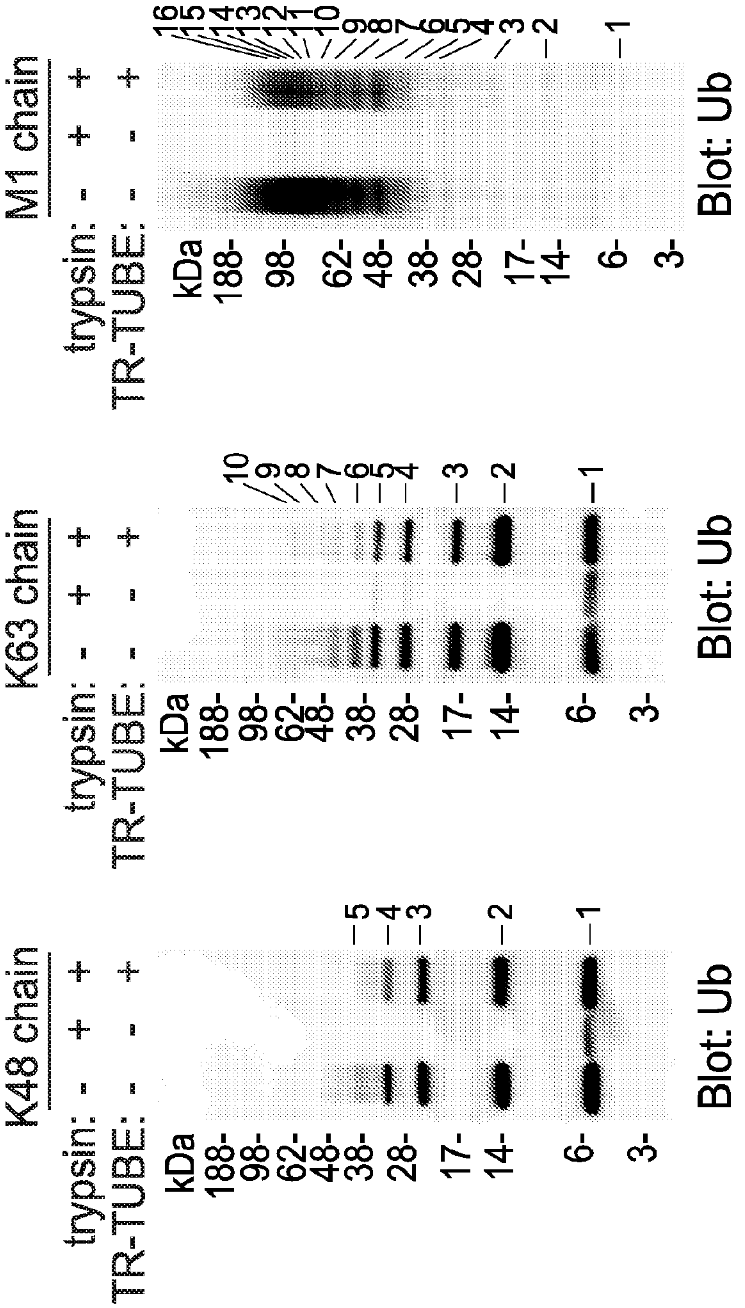

FIG. 6: Ub-ProT assay of free polyubiquitin chains.

K48-linked (left), K63-linked (middle), and M1-linked (right) polyubiquitin chains were subjected to the Ub-ProT assay. Ubiquitin was detected by western blotting with a monoclonal ubiquitin antibody. The numbers of ubiquitin molecules in the chains are labeled at right of each panel.

Figure 7:
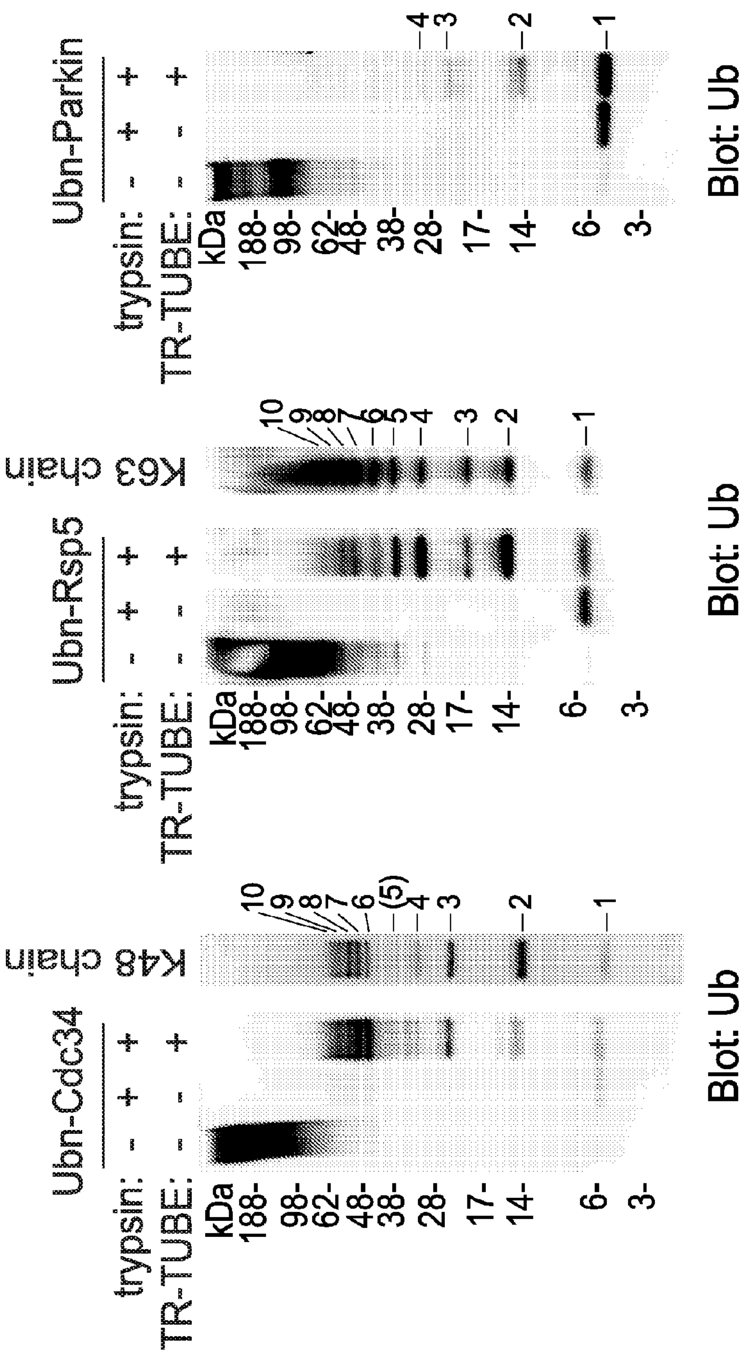

FIG. 7: Ub-ProT assay of polyubiquitylated proteins.

Self-ubiquitylated GST-Cdc34 (Ubn-Cdc34, left), self-ubiquitylated GST-Rsp5 (Ubn-Rsp5, middle), and self-ubiquitylated MBP-Parkin (Ubn-Parkin, right) were subjected to Ub-ProT assay. Free polyubiquitin chains (K48 chain and K63 chain) were used to determine the chain lengths.

Figure 8A:
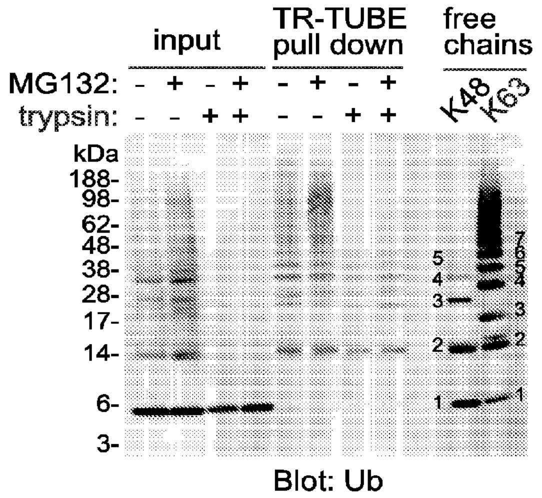
Figure 8B:
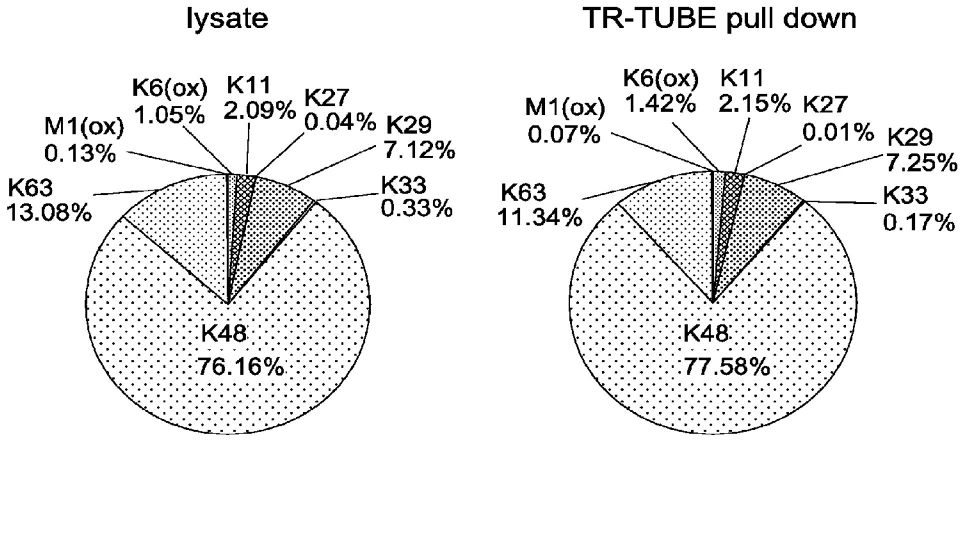
Figure 8C:
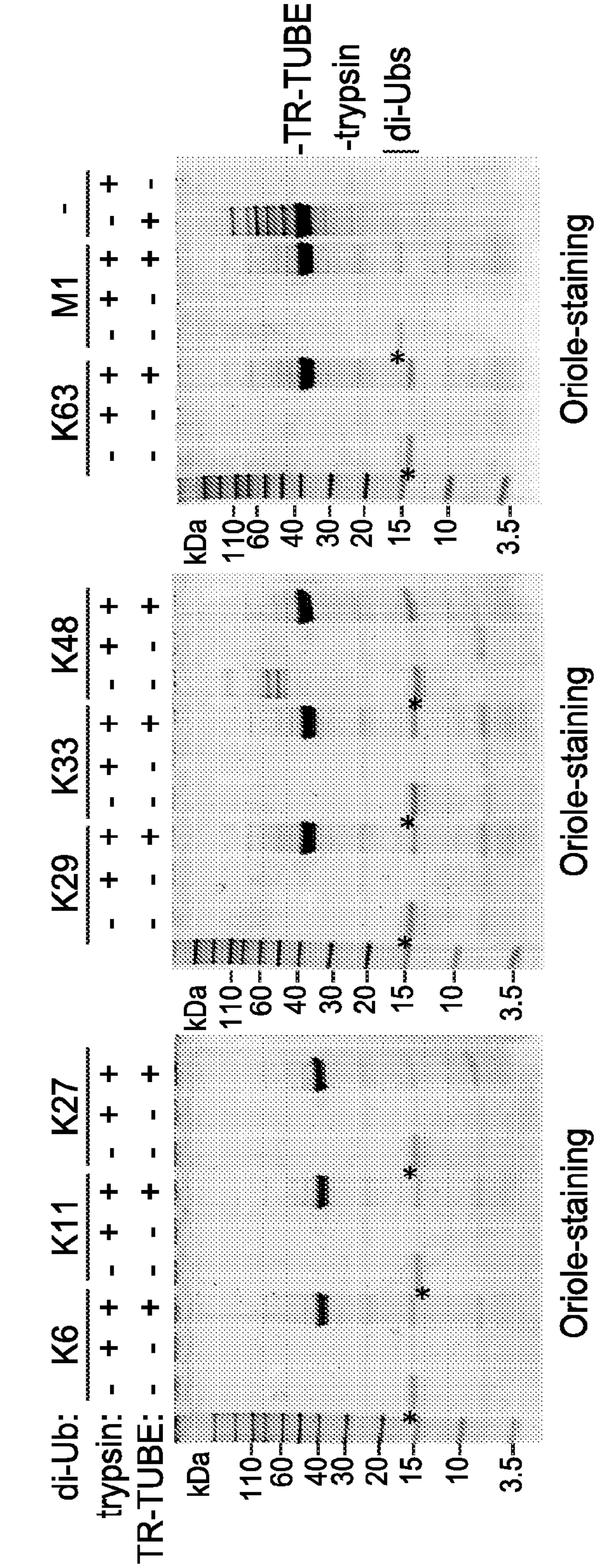

FIGS. 8A-8C demonstrate one embodiment of a Ub Pro T assay of yeast whole lysate. Ub-ProT analysis of endogenous polyubiquitylated proteins is demonstrated in FIG. 8A. Exponentially growing cells in SC medium were treated with or without 100 μM MG132 for 4 h. Polyubiquitylated proteins in the lysates were captured by TR-TUBE and subjected to trypsinization. Free polyubiquitin chains were used as a marker. Representation of ubiquitin linkages from yeast lysate and TR-TUBE-bound proteins (FIG. 8B). The individual ubiquitin chains in MG132-treated wild-type cells and samples pulled down with TR-TUBE were quantitated by mass spectrometry. Proportions of ubiquitin linkages are represented by pie charts (mean; n=3 biological replicates). Ub-ProT assay of di-ubiquitins. Di-ubiquitin (500 ng) linked through K6, K11, K27, K29, K33, K48, K63, or M1 was incubated with TR-TUBE (5 μg) and trypsin (50 ng) overnight at 37° C. (FIG. 8C). Proteins were subjected to SDS-PAGE and visualized by Oriole staining. Di-ubiquitins are marked with asterisks.

Figure 9A:
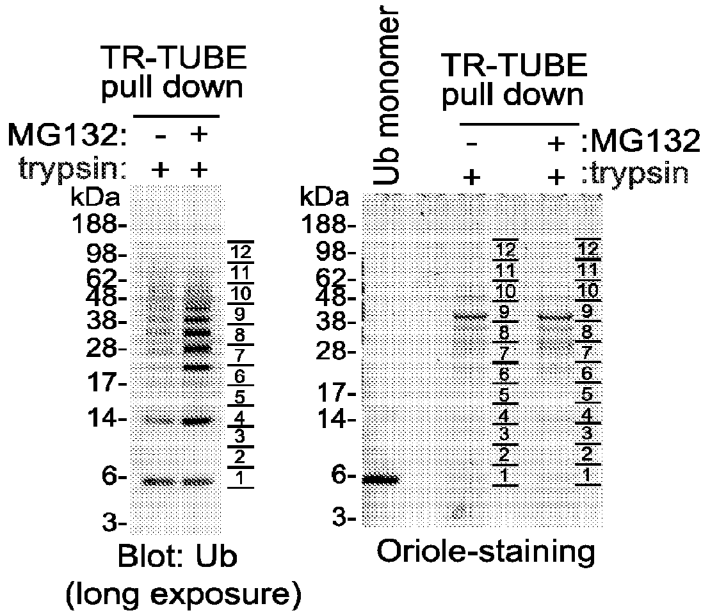
Figure 9B:
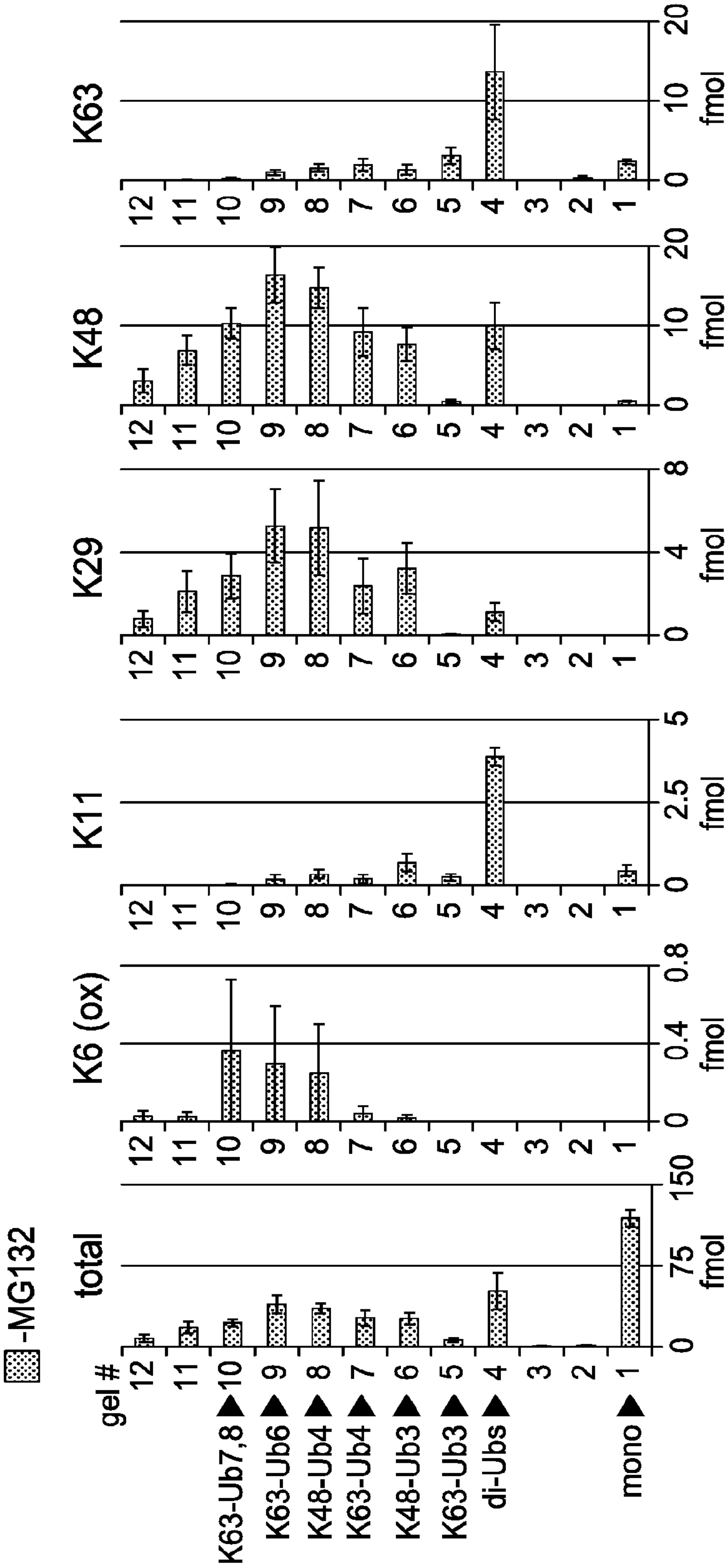
Figure 9C:
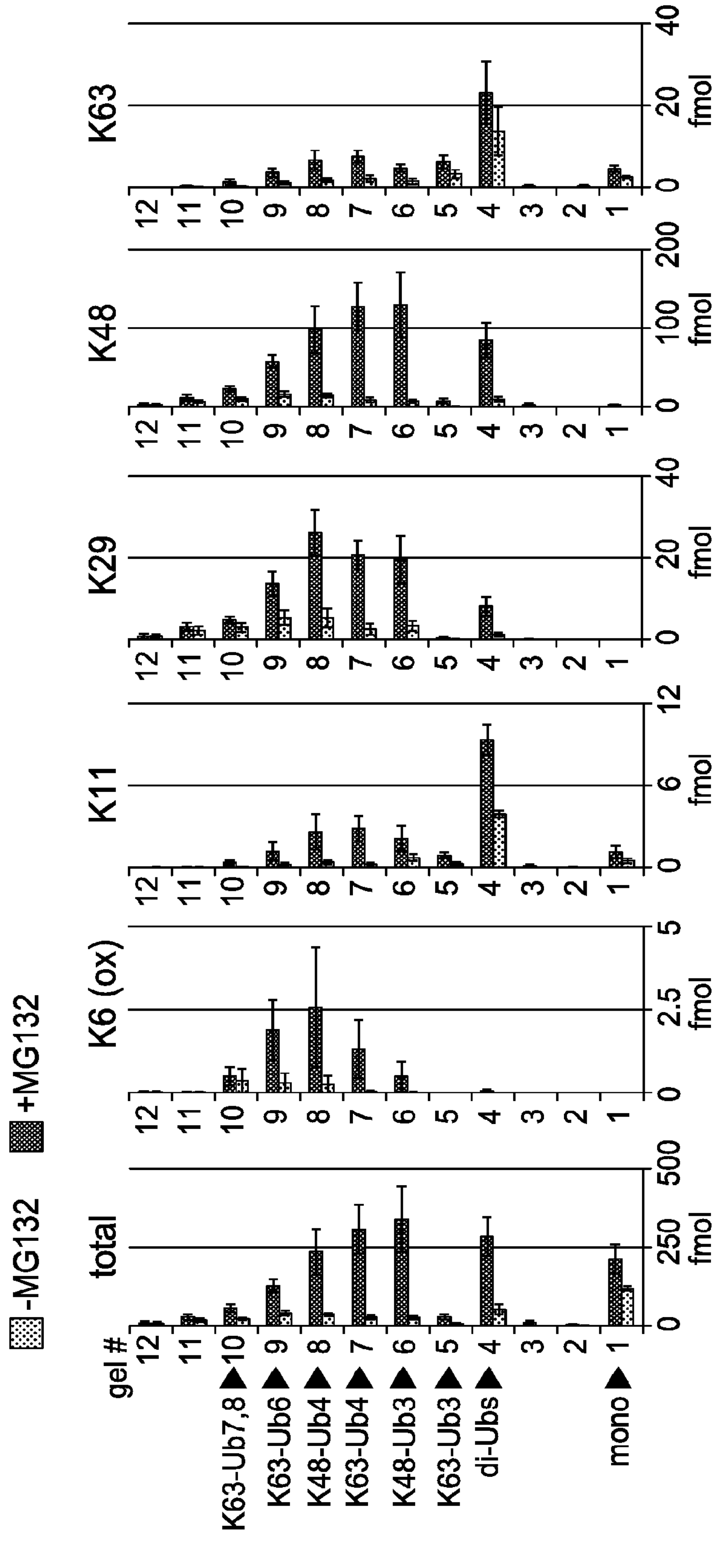

FIGS. 9A-9C demonstrate length and linkage contents of substituted attached polyubiquitin chains in cells at steady state and in cells treated with a proteasome inhibitor. FIG. 9A demonstrates ubiquitin ladders of substrate-attached polyubiquitin chains. Long exposure of western blot (left) and protein staining (right) of the Ub-ProT sample in FIG. 8A. Gel regions subjected to MS quantitation are indicated by numbers between horizontal lines. The position of the ubiquitin monomer was defined as gel fraction #1. FIG. 9B demonstrates length distributions of total ubiquitin and five major ubiquitin linkages in steady-state cells. Gel fractions in (b) were analyzed by a quantitative mass spectrometry (mean±s.e.m.; n=3 biological replicates). Relative positions of K48- and K63-linked chains are labeled at left. FIG. 9C demonstrates a comparison of ubiquitin chain lengths in MG132-treated cells.

Figure 10:
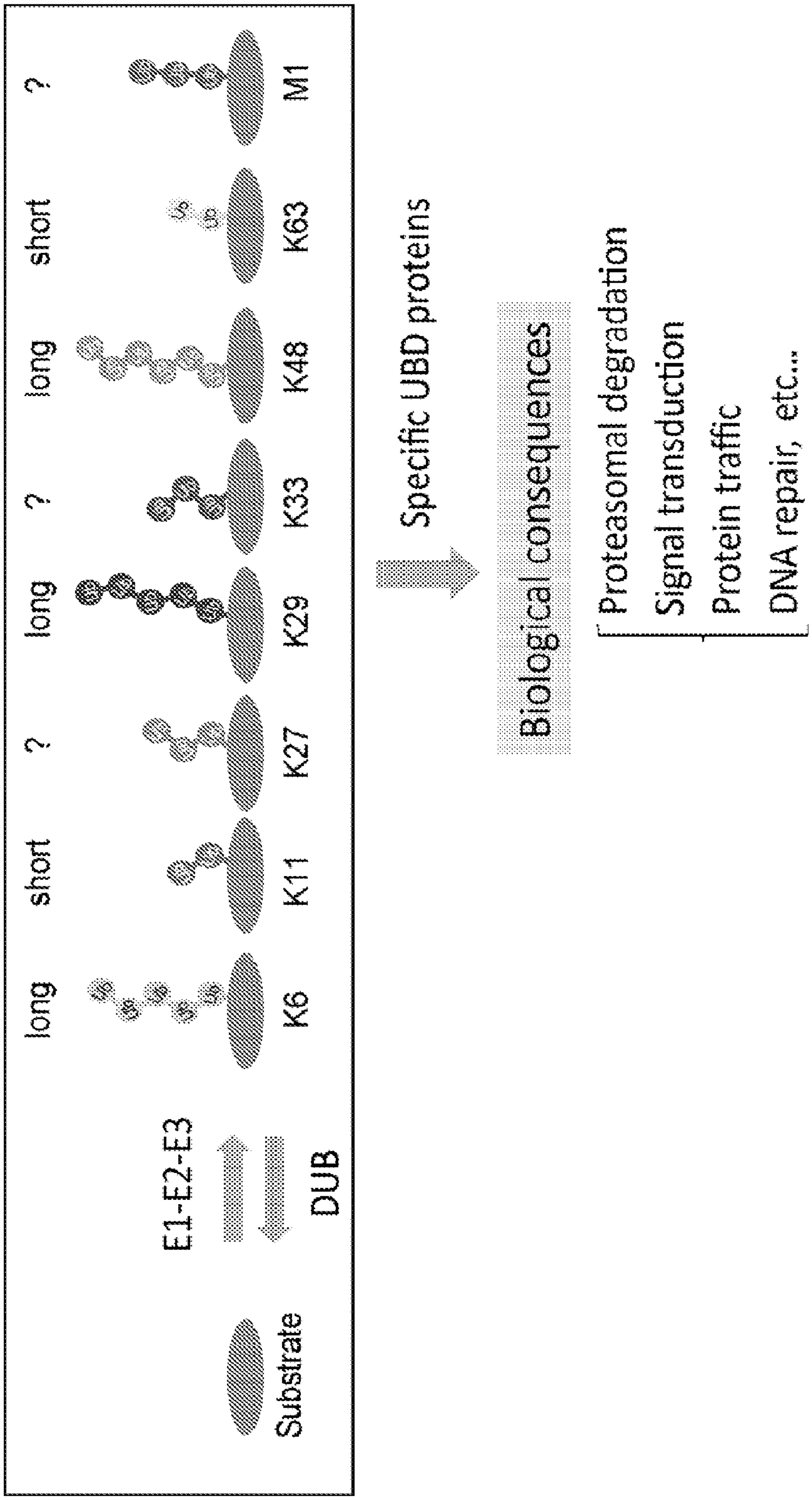

FIG. 10: Functional units of polyubiquitin chains in the cells.

Protein ubiquitylation is in equilibrium determined by the relative activities of E1-E2-E3 ubiquitin enzymes and antagonizing deubiquitylating enzymes. In rapidly growing cells, steady-state lengths of individual polyubiquitin chains are as follows: K6-, K29-, and K48-linked chains are long, whereas K11- and K63-linked chains are short. Note that the former linkage group might be involved in complex chains such as branched or mixed ubiquitin chains, although their actual levels are currently unknown. The ubiquitin chain topologies built on various substrates lead to diverse biological consequences via specific UBD proteins.

DETAILED DESCRIPTION OF THE INVENTION

The inventors of the present invention have developed a new effective tool for the method for determining ubiquitin chain length by means of generating polypeptides comprising ubiquitin binding domains which possess trypsin-resistance.

In the first aspect, the present invention relates to a polypeptide comprising ubiquitin binding domains, wherein said ubiquitin binding domains are linked to each other via a linker amino acid sequence, and wherein the ubiquitin binding domains are protected from trypsinization. In other words, the present invention in the first aspect relates to a polypeptide comprising ubiquitin binding domains, wherein said ubiquitin binding domains are linked to each other via a linker amino acid sequence, and wherein the ubiquitin binding domains are trypsin-resistant.

Hereinafter, the above polypeptides are sometimes called as TR-TUBE (trypsin-resistant tandem ubiquitin binding entity).

The TR-TUBE preferably contains four to eight ubiquitin binding domains. In addition, the TR-TUBE more preferably contains five to eight ubiquitin binding domains. Furthermore, the TR-TUBE even more preferably contains six to eight ubiquitin binding domains. Moreover, the TR-TUBE most preferably contains six ubiquitin binding domains.

In a particular embodiment of the present invention, the ubiquitin binding domain is preferably selected from a group consisting of an Uniquitin-Associated domain (UBA domain), UIM (Ubiquitin Interacting Motif), MIU (Motif Interacting with Ubiquitin) domain, DUIM (double-sided ubiquitin-interacting motif), CUE (coupling of ubiquitin conjugation to ER degradation) domain, NZF (Np14 zinc finger), A20 ZnF (zinc finger), UBP ZnF (ubiquitin-specific processing protease zinc finger), UBZ (ubiquitin-binding zinc finger), UEV (ubiquitin-conjugating enzyme E2 variant), PFU (PLAA family ubiquitin binding), GLUE (GRAM-like ubiquitin binding in EAP45), GAT (Golgi-localized, Gamma-ear-containing, Arf-binding), Jab/MPN (Jun kinase activation domain binding/Mpr1p and Pad1p N-termini), UBM (Ubiquitin binding motif) and a Ubc (ubiquitin-conjugating enzyme), functionally equivalent variant of the aforementioned ubiquitin binding domains, and combinations thereof.

The functionally equivalent variant of the aforementioned ubiquitin binding domains preferably possesses a polypeptide sequence having 90% or more homology, and more preferably, 95% or more homology with the polypeptide sequence of UBA, UIM, MIU, DIUM, CUE, NZF, A20 ZnF, UBP ZnF, UBZ, UEV, PFU, GLUE, GAT, Jab/MPN, UBM, or Ubc.

In a particular embodiment of the present invention, said linker amino acid sequence is preferably a flexible linker sequence. In addition, said linker amino acid sequence is more preferably GGGSGGG (SEQ ID NO:3).

Said polypeptide is able to further comprise at least one of tag amino acid sequences. Furthermore, said tag is preferably selected from a group consisting of a detection tag, a purification tag, and combinations thereof. Moreover, the tag is more preferably selected from a group consisting of a biotin tag, a polyhistidine tag, a flag tag and a combination thereof.

Said ubiquitin binding domains of said polypeptides are able to be the same or different. In addition, said polypeptides can comprise a polypeptide sequence having 90% or more homology, and more preferably, 95% or more homology with the polypeptide sequence represented by SEQ ID No:1. Furthermore, the polypeptide sequence is preferably a polypeptide sequence represented by SEQ ID No:1.

In the second aspect, the present invention relates to a polynucleotide comprising a polynucleotide sequence having 90% or more homology, and more preferably, 95% or more homology with the polynucleotide sequence represented by SEQ ID No: 2. In addition, the polynucleotide sequence is preferably a polynucleotide sequence represented by SEQ ID No: 2. Furthermore, the polynucleotide sequence can be a polynucleotide sequence encoding any one of the above polypeptides.

In the third aspect, the present invention relates to a gene construct comprising the above polynucleotides described in the second aspect of the present invention. In addition, the gene construct can be a gene construct encoding any one of the above polypeptides.

In the fourth aspect, the present invention relates to an expression vector comprising the above gene construct described in the third aspect of the present invention. Said expression vector preferably possesses the gene construct which is operatively bound to transcription, and optionally translation, control elements. In addition, said expression vector preferably contain the gene construct, expression thereof can be externally controlled. Furthermore, the expression of said gene construct is more preferably externally controlled by using IPTG.

In the fifth aspect, the present invention relates to a method for determining ubiquitin chain length using the above polypeptides (TR-TUBEs). The method for determining ubiquitin chain length preferably comprises: (i) preparing a mixture of an analyte and at least one of the above polypeptides (TR-TUBEs), (ii) digesting the mixture with a protease to form a digested mixture, and (iii) analyzing the digested mixture. Said protease used in the above method for determining ubiquitin chain length is preferably trypsin.

The digested mixture is preferably analyzed by electrophoresis, and the digested mixture is more preferably analyzed by western blotting analysis. In addition, an anti-ubiquitin antibody is preferably used in the western blotting analysis.

A proteasome inhibitor is preferably contained in the mixture of above (i). In addition, the proteasome inhibitor is preferably MG132.

In the sixth aspect, the present invention relates to a host cell comprising: (i) at least one of the above polynucleotides; (ii) at least one of the above gene constructs; or (iii) at least one of the above expression vectors. In addition, said host cell is preferably a bacterial cell.

In the seventh aspect, the present invention relates to a kit comprising at least one of the above polypeptides (TR-TUBEs). Furthermore, the kit is able to further comprise a solid support.

EXAMPLES

The present invention will be described below in further detail using Examples. However, the present invention is not limited to the following Examples.

Materials and Methods

Yeast Strains and Media

*S. cerevisiae* strains used in this study are isogenic to W303 strain. Standard genetic techniques were used to manipulate yeast strains. The deletion mutant of PDR5 (YYS1325) was used to increase sensitivity to the proteasome inhibitor MG132. Yeast cells were grown in SC medium (0.67% yeast nitrogen base without amino acids, 0.5% casamino acids, 2% glucose, 10 mM potassium phosphate [pH 7.5], 400 mg/l adenine sulfate, 10 mg/l uracil, and 20 mg/l tryptophan) or SC-Ura medium at 28° C.

Construction, Protein Expression, and Purification of Trypsin Resistant (TR)-TUBE The UBA domain of human UBQLN1 (NM_013438.4) was cloned into the vector pBlueScript KS (Agilent Technologies), and three Arg residues of the UBA domain were mutated to Ala using the QuikChange site-directed mutagenesis kit (Stratagene). The EcoRV site was also mutated for further construction. Six tandem copies of the UBA domain with a flexible linker sequence (GGGSGGG, SEQ ID NO:3) were cloned into vector pRSET-A (Life Technologies), in which a Cys residue was introduced upstream of the hexahistidine tag for biotinylation. The protein-coding sequence of TR-TUBE is shown in FIG. 4. TR-TUBE was expressed in *E. coli Rosetta*2 (DE3) with 0.1 mM IPTG for 15 h at 22° C. Cells were lysed by passage through a precooled French pressure cell (Ohtake Works) in lysis buffer (50 mM sodium phosphate, 300 mM NaCl, 10% glycerol, 1 mM Tris [2-carboxyethyl] phosphinehydrochloride, pH 7.0), and the lysate was clarified by 30-min centrifugation at 29,300×g. The supernatant was incubated with TALON resin (Clontech), and TR-TUBE was eluted with elution buffer (50 mM sodium-HEPES [pH 7.1], 100 mM NaCl, and 0.2 M imidazole). Then, TR-TUBE was biotinylated with EZ-link Maleimide-PEG2-Biotin (Thermo Scientific) according to the manufacturer's instructions, and further purified by gel filtration on Superdex 75 10/100 GL (GE Healthcare), preequilibrated with 50 mM HEPES (pH 7.5), 100 mM NaCl, and 10% glycerol. Biotinylated TR-TUBE was used throughout the study unless otherwise noted.

Preparation of Polyubiquitin Chains and Ubiquitylated Proteins

K48- and K63-linked polyubiquitin chains and di-ubiquitins were purchased from Boston Biochem. M1-linked polyubiquitin chains were prepared by a method described in *The EMBO journal* 25, 4877-4887, (2006) with modifications. Self-ubiquitinated GST-Cdc34 was prepared by incubating 100 μg/ml GST-Cdc34 on glutathione Sepharose beads 4B (GE Healthcare) in the presence of 33 μg/ml human His6-E1 (Boston Biochem), 500 μg/ml bovine ubiquitin (Sigma) in 20 mM Tris-HCl (pH 7.5), 10 mM $MgCl_2$, 0.1 mM DTT, and 2 mM ATP for 15 h at 37° C., as described in *Nature cell biology* 4, 725-730, (2002). Self-ubiquitylation of GST-Rsp5 was carried out by incubating 50 μg/ml GST-WW-HECT on glutathione Sepharose beads 4B in the presence of 6.25 μg/ml human His6-E1, 50 μg/ml Ubc4, 500 Kg/ml ubiquitin in 50 mM sodium-HEPES (pH 7.5), 100 mM NaCl, 10% glycerol, 10 mM $MgCl_2$, 1 mM DTT, and 5 mM ATP for 15 h at 28° C. Self-ubiquitylated MBP-Parkin was prepared by incubating 20 Kg/ml MBP-Parkin on Amylose resin (New England BioLabs) in the presence of 1.6 μg/ml human His6-E1, 100 μg/ml Ubc4, 50 Kg/ml ubiquitin in 50 mM Tris-HCl (pH 8.8), 2 mM $MgCl_2$, 2 mM DTT, and 4 mM ATP for 3 h at 32° C., as described in *The Journal of biological chemistry* 281, 3204-3209, (2006). After the reactions, the beads were washed with PBS plus 0.05% Tween 20 (PBS-T) and stored at 4° C.

SDS-PAGE and Western Blotting

Proteins were separated by SDS-PAGE on 4-12% NuPAGE Bis-Tris gels with MES buffer (Life Technologies) and visualized with Oriole fluorescent gel stain (BioRad) or Bio-Safe Coomassie Stain (BioRad). For western blotting, proteins were blotted onto PVDF membrane (GE Healthcare) using the NuPAGE immunoblotting system (Life Technologies). The membranes were probed with anti-ubiquitin monoclonal antibody (P4D1, HRP conjugated, Santa Cruz Biotechnology). Note that ubiquitin monomer was detected at ~5 kDa in this electrophoresis system.

Ubiquitin Protection from Trypsinization (Ub-ProT) Assay for In Vitro Substrates Because trypsin sensitivity of proteins varies with their structural properties, the amount of trypsin was titrated in each experimental setup. For free ubiquitin chains, polyubiquitin chain mixtures (500 ng), modified sequencing-grade trypsin (100 ng, Promega), and TR-TUBE (5 μg) were incubated in 20 μl of 50 mM ammonium bicarbonate (AMBC) supplemented with 0.01% Rapigest SF (Waters) overnight at 37° C. For self-ubiquitylated substrates, ubiquitin conjugates on beads (1 μg), trypsin (300-500 ng), and TR-TUBE (5 μg) were incubated in 20 μl of 50 mM AMBC plus 0.01% Rapigest SF overnight at 37° C. The reaction was quenched by addition of 3× NuPAGE LDS sample buffer.

Ub-ProT Assay for Yeast Lysates

For Ub-ProT assay of yeast extracts, 30 $OD_{600}$ units of log-phase cells were harvested and lysed with glass beads in 300 μl of lysis buffer (50 mM Tris-HCl [pH 7.5], 100 mM NaCl, 10% glycerol, 10 μM MG132, 10 mM iodoacetamide, and 1× complete protease inhibitor cocktail [Roche, EDTA-free]). After centrifugation, the supernatant (100 μg) was incubated with TR-TUBE (10 μg) for 1 h at 4° C. Next, TR-TUBE-bound polyubiquitylated proteins were incubated with Dynabeads MyOne Streptavidin C1 (1 mg, Life Technologies) for 45 min at 4° C. The beads were washed three times with PBS-T, and then incubated in 100 μl of 50 mM AMBC, 0.01% Rapigest SF, and trypsin (1.5 μg) overnight at 37° C. The inventors of the present invention found that streptavidin was not digested by trypsin under this condition; therefore, the polyubiquitin chains were still retained on the beads via the TR-TUBE/streptavidin complex after trypsinization. After the beads were washed with PBS-T, the polyubiquitin chains were selectively eluted by 30-min incubation with 1× NuPAGE LDS sample buffer. The samples were directly subjected to electrophoresis on NuPAGE gels in order to avoid aggregation of polyubiquitin chains.

Quantitation of Ubiquitin Chains by Mass Spectrometry

Figure 1:
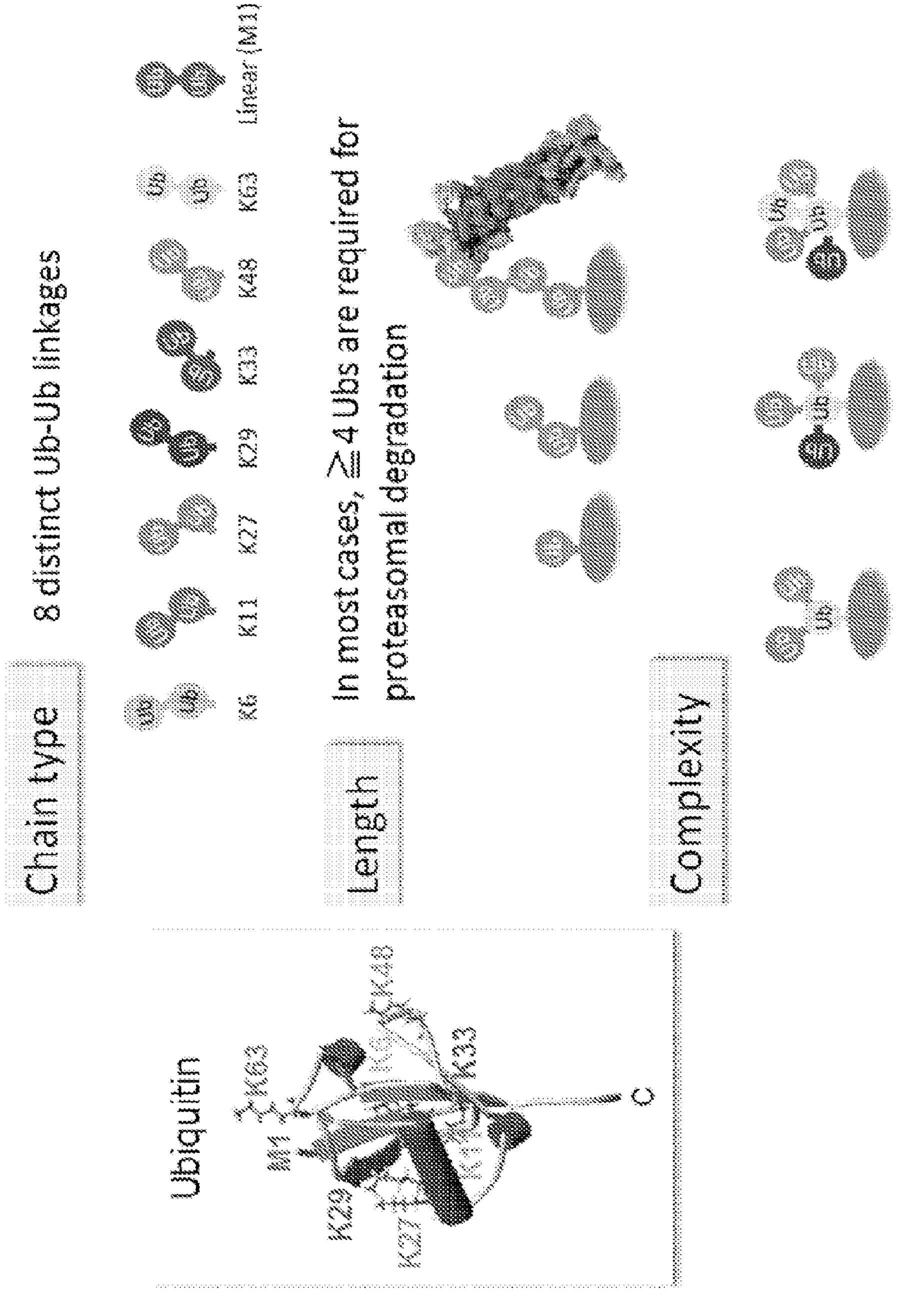
FIG. 1: Elements of polyubiquitin chains.

Ubiquitin chains were quantitated as described in *Biochemical and biophysical research communications* 436, 223-229, (2013). For ubiquitin quantitation of total lysate and samples pulled down with TR-TUBE shown in FIG. 1*d*, proteins (10 μg) were fractionated on NuPAGE gels with a short run (3 cm). The gel region corresponding to molecular weight above 62 kDa was excised, diced into 1-$mm^3$ pieces, and subjected to trypsinization. For Ub-ProT samples, proteins were fractionated by NuPAGE gels with a full run (8 cm); gel lanes were cut into 12 fractions, starting at the position corresponding to ubiquitin monomer, using a grid cutter (2 mm long×7 mm wide, Gel Company); and then subjected to trypsinization. Trypsinized peptides were extracted, spiked with nine ubiquitin AQUA peptides (M1-, K6-, K11-, K27-, K29-, K33-, K48-, and K63-linkages, as well as ESTLHVLR [EST]), and then oxidized with 0.05% $H_2O_2$ in 0.1% trifluoroacetic acid. A nanoflow UHPLC instrument (Easy nLC 1000, Thermo Fisher Scientific) was coupled on-line to a Q Exactive MS (Thermo Fisher Scientific) with a nanoelectrospray ion source (Thermo Fisher Scientific). To improve the peak shape of the K29-linkage, the peptide samples were directly loaded onto a C18 analytical column (Reprosil-Pur 3 μm, 75 μm id×12 cm packed-tip column, Nikkyo Technos Co. Ltd). Reversed-phase chromatography was performed using the Thermo EASY-nLC 1000 with a binary buffer system consisting of 0.1% formic acid (FA) (solvent A) and 100% acetonitrile/0.1% FA (solvent B) with a flow rate of 300 nl/min. For Ub-ProT samples, *E. coli* matrix (MassPREP, Waters) was added to the peptides samples (100 ng on column) to avoid nonspecific peptide adsorption. The Q Exactive MS was operated in targeted MS/MS mode, using the Xcalibur software, with time-scheduled acquisition of the nine pairs of isotopically labeled AQUA peptides/endogenous peptides in ±6 min retention-time windows. Total ubiquitin levels were calculated by EST peptide. Raw files were processed using the PinPoint software, version 1.3 (Thermo Fisher Scientific).

Example 1

A Method for Measuring Polyubiquitin Chain Length

The method of the present invention is based on the trypsin sensitivity of polyubiquitylated proteins. When polyubiquitylated proteins are subjected to trypsinization under native conditions, the substrate proteins are almost completely digested, but the polyubiquitin chains are partially digested or only cleaved at Arg74 of ubiquitin molecules, by which a signature peptide containing a di-Gly remnant of ubiquitin is produced (FIG. 3*a*). However, in the presence of a high-affinity probe for polyubiquitin chains, substrate-attached chains are protected from trypsinization; thus, the inventors of the present invention named the method 'ubiquitin protection from trypsinization' (Ub-ProT) (FIG. 3*b*). For the probe, the inventors of the present invention modified a previously reported high-affinity probe for polyubiquitin, tandem ubiquitin binding entity (TUBE) (EMBO reports 10, 1250-1258, (2009)). The original TUBE construct consists of four repeats of the ubiquitin-associated domain of human Rad23 or UBQLN1, connected with flexible linkers. The inventors of the present invention constructed trypsin-resistant (TR)-TUBE that consists of a biotin tag, hexahistidine tag, and six repeats of the UBQLN1 UBA domain in which the Arg residues were replaced by Ala residues (FIGS. 4, 5A-5C).

The inventors of the present invention first tested the method using available free polyubiquitin chains of defined lengths, linked through K48, K63, and M1 of ubiquitin (FIG. 6). The inventors of the present invention titrated the amount of trypsin and determined the smallest amount of trypsin necessary for complete cleavage of polyubiquitin chains. Under this condition, each polyubiquitin chain was cleaved into monomers or digested by trypsinization; however, in the presence of TR-TUBE, all ubiquitin chains were almost completely protected. Unexpectedly, TR-TUBE can protect M1 chains of up to sixteen ubiquitin molecules, suggesting that multiple molecules of TR-TUBE can bind with a single chain and thereby restrict trypsin accessibility. The inventors of the present invention next applied the method to self-ubiquitylated Cdc34, Rsp5, and Parkin, model substrates with distinct ubiquitylation patterns (K48-linked poly, K63-linked poly, and multiple mono, respectively) (FIG. 7). In each case, when monitored by western blotting using an anti-ubiquitin antibody, the ubiquitylated proteins were detected as a smear and were almost completely disappeared following trypsinization. By contrast, in the presence of TR-TUBE, typical ubiquitin ladders were detected after trypsinization. Comparison with free K48-linked polyubiquitins (used as a length marker) revealed that the polyubiquitin chains that had been attached to Cdc34 contained up to ten ubiquitin molecules (FIG. 7, left). In the case of polyubiquitylated Rsp5, the length of attached K63-linked chains was determined to be up to octamer (FIG. 7, middle). By contrast, Ub-ProT assay of self-ubiquitylated Parkin revealed monoubiquitin and, to a lesser extent, short ubiquitin chains (FIG. 7, right). Because TR-TUBE captured almost all the ubiquitylated Parkin (data not shown), TR-TUBE can bind multiple monoubiquitylated substrates as well as polyubiquitin chains as discussed below.

To investigate the versatility of Ub-ProT, the inventors of the present invention analyzed the linkage specificity of TR-TUBE using yeast lysate. The inventors of the present invention quantitated the individual ubiquitin linkages by parallel reaction monitoring (PRM), a MS/MS quantitation method for high-resolution mass spectrometry. PRM allowed to quantitate all the ubiquitin linkages from 100 amol to 1 pmol, even in biological complex samples. Lysate prepared from MG132-treated cells was fractionated by SDS-PAGE and the gel region corresponding to high molecular weight (>62 kDa) was excised, trypsinized, spiked with isotopically labeled peptide standards, and analyzed by ubiquitin-PRM (FIGS. 8A-8C). As reported previously, K48- and K63-linkages were detected predominantly. Remaining linkages were also clearly detected with an absolute abundance order of K29>K11>K6>M1≅K27≅K33 (FIG. 8*b*, left). The proportions of ubiquitin linkages were similar to those reported in a recent study by other group (*Molecular & cellular proteomics: MCP* 10, M111 009753, (2011)). Ubiquitylated proteins in the lysate were pulled down by TR-TUBE (FIG. 2*a*) and analyzed in the same way. The proportions of ubiquitin-linkages among TR-TUBE-captured proteins were quite similar to those in the lysate (FIG. 8*b*, right). Because the precise amount of mixed and branched chains has not been determined in the cells, TR-TUBE may bind indirectly with atypical chains. However, Ub-ProT assays against di-ubiquitin of all eight linkage types revealed that TR-TUBE protected all chains from trypsinization (FIG. 8*c*). These results suggested that TR-TUBE binds ubiquitylated proteins without any linkage preference.

Example 2

Steady-State Units of Polyubiquitin Chains

The inventors of the present invention next investigated the mean lengths of substrate-attached polyubiquitin chains in yeast lysate. To the knowledge of the inventors of the present invention, the actual chain lengths of polyubiquitylated proteins in vivo have not been previously determined. In this experiment, the inventors of the present invention used a drug-sensitive pdr5 mutant to determine the effect of a proteasome inhibitor, MG132. Exponentially growing cells were lysed with glass beads in the presence of MG132 and iodoacetamide in order to inhibit deubiquitylating enzymes. Ubiquitylated proteins in the lysate were captured and pulled down by TR-TUBE using the biotin tag. The patterns of ubiquitylated proteins were quite similar between lysate and TR-TUBE-captured proteins, with the exception of ubiquitin monomer, suggesting that TR-TUBE can capture all endogenous ubiquitylated proteins other than ubiquitin monomer (FIG. 8*a*, lanes 1 and 5). Upon trypsinization of the lysate, signals from ubiquitin conjugates completely disappeared (FIG. 8*a*, lanes 3 and 4). When the TR-TUBE-captured proteins were trypsinized, a ubiquitin-chain ladder was produced (FIG. 8*a*, lanes 7 and 8). A previous proteomics study has suggested that yeast tryptic peptides are, on average, 8.4 amino acids in length (*Journal of proteome research* 9, 1323-1329, (2010)). Thus, if the ubiquitylation sites were structurally hindered, i.e., if trypsin were unable to attack the proximal ubiquitins, the substrate-attached ubiquitin chains should converge to the individual chain sizes. It is also noted that different ubiquitin chains with three or more ubiquitins exhibited different gel mobilities (FIG. 8*a*, free chains). Comparisons with free K48-linked ubiquitin chains, used as size standards, revealed that the mean lengths of the substrate-attached ubiquitin chains were in the dimer to hexamer range.

The inventors of the present invention also quantitated the individual ubiquitin linkages in the substrate-bound ubiquitin chains of each length. Gel lanes were fractionated into 12 pieces corresponding to ubiquitin monomers and longer chains, and the fractions were subjected to Ub-PRM (FIGS. 9A-9C). Because the abundances of M1-, K27-, and K33-linkages are quite low (<0.17% of total linkages), the inventors of the present invention focused on the five major linkages in this experiment. As shown in FIG. 9*b*, the length distributions of the five major ubiquitin linkages were quite different, but they could be divided into two groups: K6-, K29-, and K48-linkages were mainly detected in the longer chains, whereas K11- and K63-linkages were mainly detected in the shorter chains. When total ubiquitin levels were quantitated by EST peptide, nearly 50% of ubiquitin was detected as the monomer (FIG. 9*b*, total). TR-TUBE did not bind ubiquitin monomer, suggesting that a significant portion of ubiquitylated proteins exist as the multiply monoubiquitylated form, consistent with the results of a previous study (*Nature methods* 8, 691-696, (2011)). Thus, at steady state, most endogenous substrates are attached to up to six ubiquitin molecules; K6, K29-, and K48-linkages are detected in longer chains, whereas K11- and K63-linked chains are mainly detected as dimers.

Example 3

Effect of Proteasome Inhibitor on Chain Length

The inventors of the present invention also analyzed proteasome inhibitor-treated cells by Ub-ProT. After treatment with 100 μM MG132 for 4 h, ubiquitylated proteins accumulated in the cells (FIG. 8*a*, lanes 1 and 2). Surprisingly, the Ub-ProT assay suggested that signal intensities of the ubiquitin ladder were increased, but the chain length was not changed (FIG. 9*a*, left). The inventors of the present invention quantitated the ubiquitin linkages from the ubiquitin ladder; compared to untreated cells, proteasome-inhibited cells accumulated all types of linkages. K6-, K29-, and K48-linked chains accumulated at high levels, but their length distributions were unchanged. Furthermore, long K11- and K63-linked chains accumulated slightly in the proteasome inhibitor-treated cells (FIG. 9*c*). It will be of great interest to determine whether the long K11- and K63-linked chains are homogeneous. Collectively, these results suggested that most proteasome substrates in cells are attached to ubiquitin chains within a length of six ubiquitins.

CONCLUSIONS

Robustness of Ubiquitin Length Regulation

In the 1980s, it was realized that polyubiquitin chain is a protein degradation signal for the proteasome (reviewed in *Annual review of biochemistry* 67, 425-479, (1998) and *Cell* 116, S29-32, 22 p following S32 (2004)). Subsequent in vitro studies have defined that tetraubiquitin is the minimal signal for proteasomal degradation. Nowadays, eight different ubiquitin linkages have been identified in cells, and a large number of studies have focused on the generation and decoding of ubiquitin signals in regard to chain types. However, the length of ubiquitin chains, additional key element of ubiquitylation, has not been carefully examined especially in vivo. In the present application, the inventors of the present invention established the Ub-ProT method, which can reveal the chain length of endogenous ubiquitinated proteins. Using Ub-ProT, the inventors of the present invention determined the mean lengths of substrate-attached ubiquitin chains: K6-, K29-, and K48-linked chains were mainly in the tetramer to hexamer range, whereas K11- and K63-lined chains were mainly dimers (FIG. 10). In the steady-state, these chain lengths might be functional units in cells. Surprisingly, the maximum lengths of the individual chains, up to hexamers, were not changed by either proteasome inhibition or ubiquitin overexpression. Because ubiquitin modifications are generally thought to exist in equilibrium between ubiquitylation and deubiquitylation, enhanced ubiquitylation might be predicted to cause chain elongation by overwhelming deubiquitylation. The robustness of the regulation of chain length might be due to specific UBD-containing proteins that bind and protect ubiquitin chains with appropriate lengths (probably in the 2-6-mer range) from deubiquitylating enzymes before they exert their functions, as proposed previously (*FEBS letters* 535, 77-81 (2003), *Cell* 120, 73-84, (2005)). Alternatively, the ability of ubiquitylating enzymes to elongate chains may be intrinsically limited in vivo, as suggested by a previous in vitro study (*Nature* 462, 615-619, (2009)). Because single attachment of ubiquitin costs one molecule of ATP, restriction of chain lengths would benefit the cell by reducing total energy consumption.

Collectively, the results of this study reveal the mean length of substrate-attached polyubiquitin chains and demonstrate the robustness of ubiquitin chain length regulation in cells. These findings suggest that ubiquitin chain length represents an additional layer in the regulation of ubiquitin-mediated cellular processes.

The invention claimed is:

1. An expression vector comprising a polynucleotide comprising a polynucleotide sequence having 95% or more homology with the polynucleotide sequence represented by SEQ ID No: 2.

2. The expression vector according to claim 1, wherein a gene construct is operatively bound to transcription, and optionally translation, control elements.

* * * * *